United States Patent [19]
Gil-Vernet

[11] Patent Number: 6,117,067
[45] Date of Patent: Sep. 12, 2000

[54] DEVICE FOR THE HEIGHT-ADJUSTABLE FIXING AND SUPPORT OF INTERNAL ANATOMICAL ORGANS

[76] Inventor: José Ma Gil-Vernet, Francesc Carbonell, 21-23, Barcelona Atico D 08034, Spain

[21] Appl. No.: 09/131,985

[22] Filed: Aug. 11, 1998

[30] Foreign Application Priority Data

Mar. 10, 1998 [ES] Spain ........................... 9800505

[51] Int. Cl.⁷ ........................................... A61F 2/02
[52] U.S. Cl. ................. 600/30; 600/37; 128/DIG. 25
[58] Field of Search ....................... 600/29–31, 37; 128/DIG. 25; 623/12, 14

[56] References Cited

U.S. PATENT DOCUMENTS

| | | | |
|---|---|---|---|
| 4,019,499 | 4/1977 | Fitzgerald | 128/1 R |
| 4,938,760 | 7/1990 | Burton et al. | 600/29 |
| 5,474,518 | 12/1995 | Velazquez | 600/30 |
| 5,518,504 | 5/1996 | Polyak | 600/37 |

FOREIGN PATENT DOCUMENTS

WO 96/01597  1/1996  WIPO ................. A61F 2/00

*Primary Examiner*—John P. Lacyk
*Attorney, Agent, or Firm*—Darby & Darby

[57] ABSTRACT

The present invention comprises a device for adjusting the height and supporting internal anatomical organs. The device comprises a chamber having elastic properties, the volume of which varies in accordance with the amount of fluid in the container. To increase or decrease the volume, a capsule connected by a tube to the container is provided which is adapted to be located near the skin of the patient. A hypodermic needle can extract or introduce fluid into the capsule thereby to change the volume of the chamber. A thread is connected to one base of the chamber and the other base is adapted to sit on an anatomical region in the body. The thread is adapted to surround the selected organ whereby changes in the volume of the chamber changes the distance between the bases thereby to move the organ.

14 Claims, 5 Drawing Sheets

DEVICE FOR THE HEIGHT-ADJUSTABLE FIXING AND SUPPORT OF INTERNAL ANATOMICAL ORGANS

BACKGROUND OF THE INVENTION

1. Field of the Invention

The present invention is intended to disclose a device for the height-adjustable fixing and support of internal anatomical organs, by means of which it is possible to effect in a very simple manner the securing of internal anatomical structures and organs when they are positioned in the desired position by the surgeon, additionally having properties of adjustment in height as required.

As is already known, in operating practice there are situations in which the surgeon wishes to position and ensure the securing of internal anatomical organs at a certain height with respect to specific references of the human body, for the purpose of completing the operation carried out and/or in order to perform organic functions, making good certain bodily functions or assisting them.

One of the fields of more specific application of the device which is the subject of the present invention will be that of urinary tract surgery, in particular urinary tract surgery concerned with the correction of urinary incontinence.

2. Description of the Related Art

In particular, the object of the present invention is to ensure a complete cure for severe urinary incontinence in women, which has been repeatedly operated on without success with the conventional surgical techniques, since at present no method has been described which ensures a cure for this.

The problem of urinary incontinence is one of the most widespread nowadays, the attempt to propose effective remedies in order to try to reduce its effects being very costly. For example, in North America, according to CARL G. KLUTKE of the Urology Department of the University of Washington, incontinence affects more than twenty million people and more than half the admissions to chronic centres and an annual expense of a billion dollars for absorbent devices and others are attributed to it.

Moreover, the said problem is increasing with the expectation of greater longevity of the population. Increasing costs are assumed which become insupportable for the various health administrations of each country.

In particular, the treatment of female urinary stress incontinence continues to be a formidable task for the health community, according to what is stated by C. G.KLUTKE in his publication "Female stress incontinence in the 90's". Considerable efforts have been made, but it is necessary to understand the problem better and achieve a more effective treatment. The surgical treatment of this ailment will continue to be an important feature of urology. The enthusiasm for new innovative surgical approaches should be weighed against objective evidence of results and with a clear understanding of the morbidity involved.

Multiple vaginal deliveries, removal of the uterus, and menopausal vaginal changes are factors which contribute to prolapse and to urinary stress incontinence in women.

The involuntary loss of urine may occur by means of two mechanisms which, for the moment, require different surgical techniques for their correction. The most common is the descent or dropping of the neck of the urinary bladder and of the urethra (hypermobile urethra).

The other is due to the fact that the urethra has lost its closure capacity (deficiency of the internal sphincter). In men, incontinence is produced by lesion of the external sphincter in the course of operations on the prostate.

More than a hundred surgical techniques for the correction of incontinence have been described. The large number of procedures proposed demonstrates that the problem persists. The percentage of failures is very high and increases with the passage of time, as attested by the most recent publication of Stefan Conrad of the University of Hamburg (J. Urol. No. 1 32–37, 1998), who presents the long term results (5 years) of the Stamey suspension intervention, which is the treatment of choice for stress incontinence in women, and in which he emphasises that the failure rate is 50% out of a total of 130 patients evaluated.

When the neck of the bladder and the urethra are found to have descended, the object of surgery is to return them to their original anatomical position; in order to achieve this, it is necessary to displace these structures upwards and forwards, and they have to be raised behind the pubis.

The treatment of defective functioning of the sphincter of the urethra causing urinary incontinence is linked to achieving greater urethral resistance, which is obtained either by means of a sling suspending the neck of the bladder, or by the reconstruction of the said neck, or also by means of periurethral injections of polytetrafluorethylene or by means of an artificial urinary sphincter.

The procedure based on the sling suspending the neck of the bladder is relatively simple and offers certain advantages over the remaining procedures. Many procedures based on the technique of the suspension sling are known and have been described since the beginning of this century.

The ALDRIDGE technique is classic and has remained for many years the most frequently employed. Another similar technique was described by MOIR and in 1984 POLLACK and his associates described the use of tendons and aponeurosis as a sling for suspending the neck of the bladder when connecting it with the COOPER ligament.

Another suspension procedure was described by BEY-DEREV of the Centre for the Treatment of Incontinence, of Irvine University in California. This consists of a percutaneous procedure which makes it possible to capture with a threaded needle a maximum portion of the mobile part of the pubocervical fascia and of the tissues situated laterally and on both sides of the neck of the bladder and of the urethra, the suspension of the said neck being achieved by means of anchorage of the ends of the aforesaid lateral suspension threads on two points of the pubic bone. These suspension threads are tensioned and fastened in a first intervention to these anchorage points inserted into the bone. But it is clear that the initial tension imparted to the aforesaid suspension threads cannot be adjusted easily nor modified afterwards after time has lapsed since the urological intervention.

The great problem which arises in all the surgical procedures described is to know to what precise degree the neck of the bladder should be raised and positioned or the precise degree of compression of the urethra in order to guarantee the correction of the incontinence and to obtain normal micturition. Because if the surgeon exceeds it by raising the urethro-vesical union a few millimetres more or extensively compresses the urethra, a urinary obstruction will be produced, a frequent complication which renders repeated or permanent explorations necessary. On the other hand, if by default the surgeon falls short in the lifting or compression of the urethra, then the incontinence will soon reappear.

There is no test or proof available which makes it possible to know this, that is to say, there are no parameters for determining the appropriate degree of tension for the fixing of the sling. This crucial moment of fastening the two sutures which support and raise the neck of the bladder and the urethra depends on subjective appraisal or empirical determination on the part of the surgeon; it is more art than science. But even accepting that the appropriate point of elevation of the urethro-vesical union or that of compression of the urethra has been found, and the two objectives have been achieved, that of curing the incontinence and that of restoring normal micturition, it is not known for how long this situation will last or persist, since it is rarely permanent or definitive and this is because the correction mechanisms fail or because the tissues fail through the natural process of involution or ageing. The urethral closure pressure (sphincter) declines markedly with age, or in the course of life an illness may occur (bronchitis, asthma) which entails an increase in the intra-abdominal pressure which strains the containment system created and the incontinence reappears.

More recently, endeavouring to overcome this indeterminate adjustment of the effect of suspension of the neck of the bladder, various mechanical adjustment procedures have been proposed. But these procedures require the establishment, during the intervention and on the abdomen of the patient, of mechanical adjustment means, either a single one located in the central part and on which the lateral suspension threads are joined, or by means of two lateral adjustment mechanisms generally formed, in both cases, by screw-threaded parts which can be adjusted manually from outside above the abdomen of the patient. These adjustment mechanisms remain on the one hand inside, and on the other hand outside the abdomen of the patient after the urological operation and for several days, with a risk of infection, until the adjustment operations are deemed to have been completed. Then, the said adjustment mechanisms have to be separated from the body and the retaining means or final anchorage of the ends of the said threads arranged, in order, finally, for the said open wounds at the anchorage points to be covered by the corres-ponding adipose tissue and the skin in order to cover up the incisions made, as well as the aforesaid fixed retain-ing means for the ends of the suspension threads.

It will be understood that after all these operations have been carried out, further mechanical adjustments will not be possible except by means of further surgical interventions.

But, in practice, further adjustments of the tension of the sling are always necessary, since the tensioning threads stretch in different proportions after the urological intervention or simply when the tissues suffer certain structural changes after a period of time.

This plethora of procedures described in the medical technical literature confirms the non-existence of ideal methods.

As already stated, the principal reason for the difficulties encountered for the suspension sling procedure is the impossibility of obtaining easy control of the tension of the suspension threads thereof.

According to what was published in the Journal of Urology (Vol. 14, January 1989), some doctors, researchers of the Nagoya University School Department of Urology, state that the tension of the threads of the sling has not been quantified either for the genuine incontinence stress or for the neurogenic bladder.

In spite of the popularity of the system of suspension of the neck of the bladder, no articles have appeared which have mentioned and quantitatively specified the degree of tension which should be imparted to the suspension threads of the sling at the moment when they are tied to a rela-tively fixed retaining part.

The stretching of the threads is generally understood to be between 4 and 8 per cent after a period of 70 days, depending on their initial tension.

The result of this ambiguity is frequently manifested in transitory or definitive retention or difficulty in urinating if the threads have been tied with too much tension at the end of the intervention, or in persistent incontinence if the opposite occurs.

BRIEF SUMMARY OF THE INVENTION

The present invention is intended precisely to remedy the drawbacks previously mentioned, both in the correction of incontinence in cases where the neck of the bladder and the urethra have descended, and in those where the cause is deficiency of the internal sphincter of the urethra, the present invention providing the means for correct anatomical positioning of the organs in a very simple manner, unaggressive from the operating standpoint, and which also has a capacity for adjustment, for life, and without the need to have recourse to a further operation.

In order to achieve its objectives, the device which is the subject of the present invention comprises a unit in the form of an elastic chamber, expansible by the action of a fluid contained within it and which is intended to be surgically incorporated in the most anatomically appropriate place so that use may be made of the said unit for fixing at the desired height the internal anatomical organs which are the subject of the surgical intervention and in such a manner that, given the elastic properties of the said unit, it is possible to act on it, effecting its selective deformation by the action of the fluid contained in the elastic chamber, for the purpose of producing controlled displacement of the anchorage points of the internal means for securing the anatomical organs, principally constituted by fine, strong cables of biologically compatible materials.

In order to obtain greater efficiency in the control of the height of suspension which the device provides, the unit deformable by the action of the fluid will have differentiated characteristics of rigidity in its structure, so that the action of the fluid inside the said unit is basically manifested in a variation in the height of the elastic unit, it thus being possible to exploit to the optimum degree the effect of adjustment on introducing or extracting specific amounts of control liquid. For this purpose, the elastic unit will basically comprise a chamber with a lower wall or base intended to sit in the most suitable place, selected from the anatomical standpoint, and an upper face or upper base carrying the connections to the threads for the suspension and fixing of the anatomical organ, so that the said upper and lower bases can carry in one of the cases, preferably on its upper base, a plate of a high strength material, for example titanium, in order to improve the functioning of the chamber and permit easy and strong fastening of the ends of the threads for the suspension of the anatomical organ or organs.

In order to permit the placing of the elastic unit deformable by means of fluid in the most convenient place from the anatomical standpoint, the present invention provides for the said chamber to communicate, by means of a fine tube of biocompatible synthetic material, with a small capsule which will be coupled in a subcutaneous arrangement, but sufficiently close to the skin of the patient so that from the outside a puncture can be made with a fine hypodermic needle in order to gain access to the said control cell or capsule for the purpose of introducing or extracting liquid in the required manner to adjust the desired fixing height of the anatomical organ.

For the purpose of improving the identification of the liquid and being able to exert greater control, the liquid will preferably carry a marker or contrast of the compatible dye type.

The device of the present invention may be applicable not only as a device for the raising of the neck of the bladder and of the urethra by means of a suitable sling, but also to other operating systems which require adjustable suspension, such as that termed transvaginal colpo-suspension.

For the remainder, owing to its characteristics, the device which is the subject of the invention will be applicable to a wide range of surgical interventions not limited to interventions in women, but also in men for urological or other purposes.

BRIEF DESCRIPTION OF THE DRAWINGS

To make it easier to understand, drawings showing a preferred embodiment of the present invention are provided on an explanatory but non-limiting basis.

DETAILED DESCRIPTION OF THE INVENTION

As can be observed in the figures, the device of the present invention comprises a unit 1 having elastic properties and preferably deformable in a controlled manner from the directional standpoint, which unit, in the form of a chamber with elastic walls, is incorporated in the appropriate anatomical region in order to obtain sufficient support for its lower face, for example the muscular mass 2, being connected by means of thread-like elements of a strong and biologically compatible material, such as nylon threads 3 and 4, with a sling 5 for raising the urethral canal 6, having a tube 7 communicating with a small capsule 8 located close to the skin 9 of the patient for the purpose of permitting easy access to the said capsule by means of a hypodermic needle. The thread-like elements 3 and 4 may be constituted in a very varied manner, for example, monofilaments, braided threads, micro-chains, etc.

Figure 1:
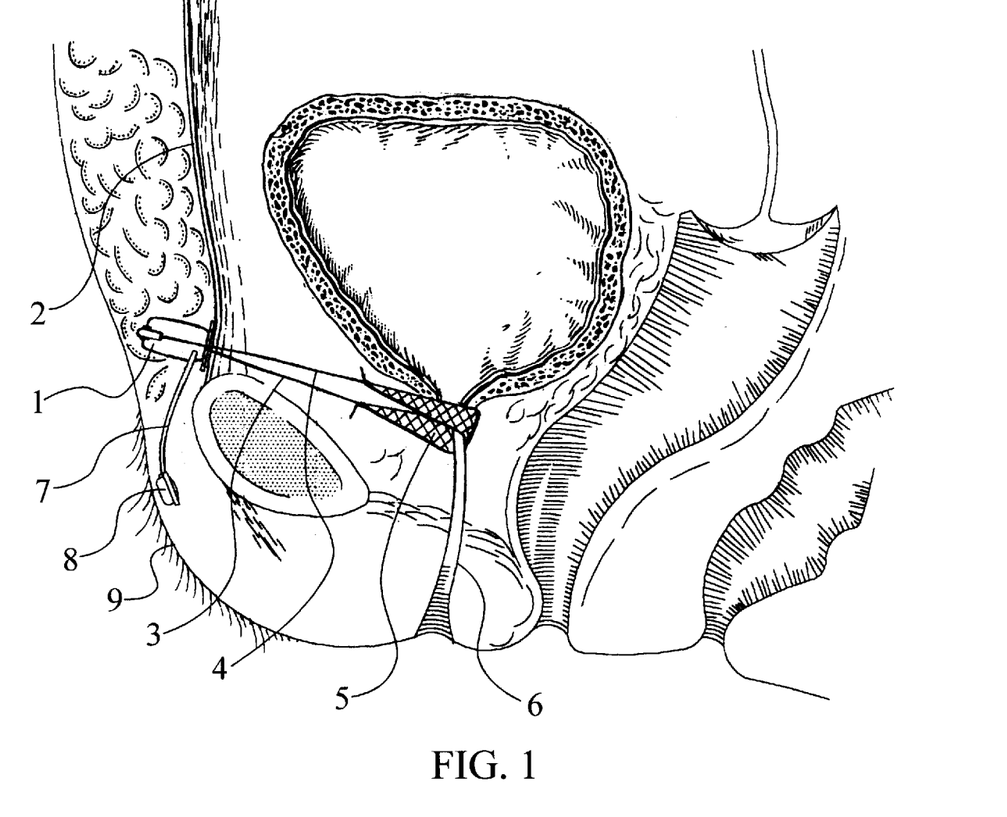
FIG. 1 shows diagrammatically an illustrative anatomical section of a characteristic form of application of the device which is the subject of the present invention.
Figure 2:
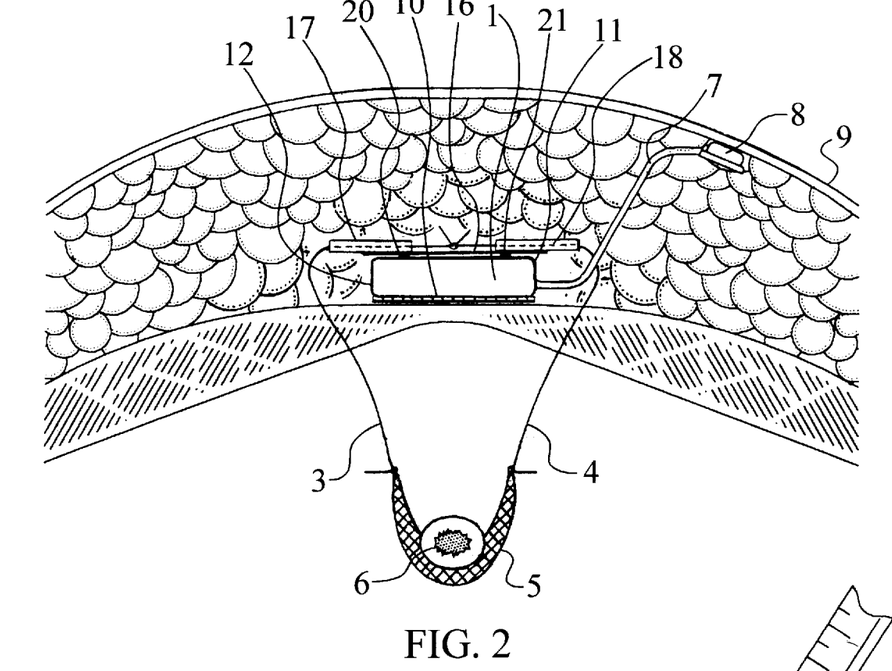
FIGS. 2 and 3 are different diagrammatic sections showing the application of the device to the suspension and adjustment in height of the urethral canal.
Figure 3:
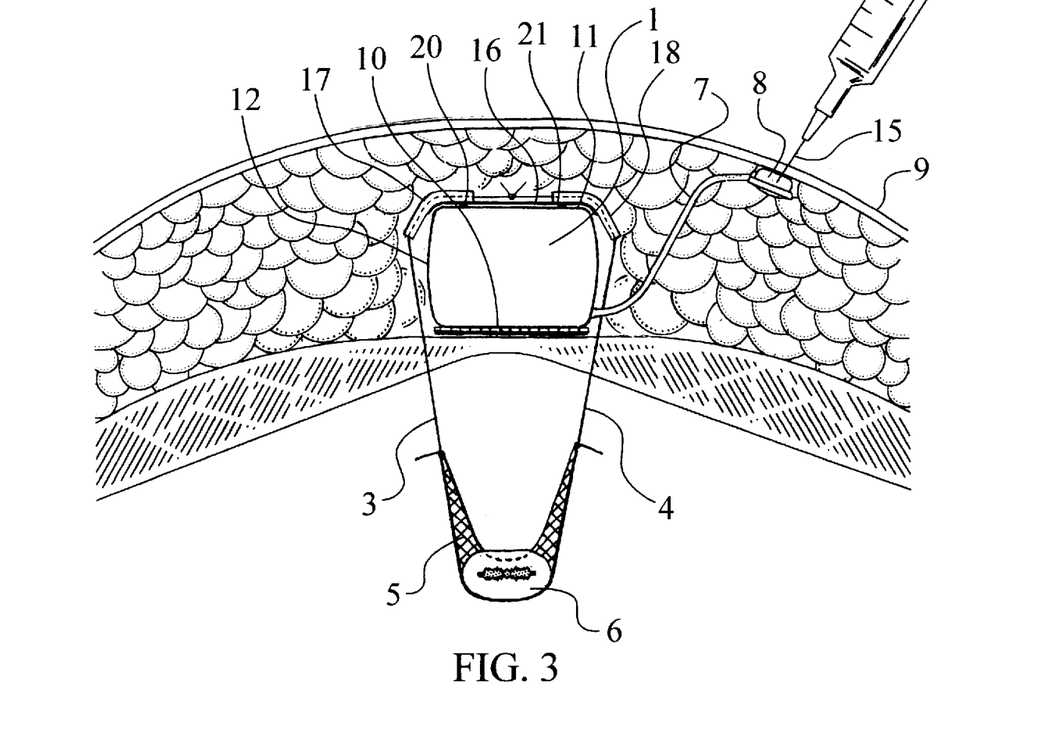

As will be seen in FIGS. 2 and 3 the chamber 1 has a lower base 10 and an upper base 11, joined by the lateral walls 12. It is a characteristic of the device which is the subject of the present invention that the chamber 1 has elastic properties, preferably unidirectional, comprising a fluid, in particular a liquid, inside it in a variable amount, so that the volume of the chamber 1 will increase or decrease as a function of the volume of liquid intro-duced, and making use of the elastic properties of the chamber. For the introduction of the liquid into the inside of the chamber 1, a tube 7 will preferably be provided, connecting the said chamber with a flattened capsule 8 arranged close to the skin of the patient which has been indicated, as in FIG. 1, by the number 9.

In order to obtain the preferably unidirectional effect in the elastic deformation of the chamber 1, the latter will preferably have the two bases 10 and 11 with characteristics of lower strength than the lateral walls 12. In this manner, the increase in volume of the chamber, as shown by way of example in FIG. 3, will preferably be manifested in a difference between the separation of the bases 10 and 11 of the chamber 1, without appreciable lateral deformation. This is intended to permit the greatest possible displacement between the aforesaid bases, that is to say, the greatest effect of height control on the connecting threads 3 and 4 for a specific amount of liquid introduced into or extracted from the chamber 1.

As already indicated, the introduction and extraction of liquid will be effected, for example, by means of a hypodermic needle 15 which will pass through the skin and the capsule 8, making it possible to introduce or extract the liquid.

The liquid used in the device which is the subject of the present invention will preferably be water or some other biocompatible liquid with a radiological contrast having a specific control coloration.

The fastening of the threads 3 and 4 to the chamber 1 in order to enable the deformation of the said chamber to be manifested in an effect of tensioning or slackening of the threads 3 and 4 can be effected in a version similar to that shown in FIG. 3, in which can be seen the fixing of the ends of the threads 3 and 4 above a strong plate 16, associated with the upper base 11 of the chamber 1, by means of bonding or welding points such as 20 and 21, the said plate being able to consist, for example, of a titanium plate which will make it possible to obtain high strength combined with extreme lightness. In order to improve the suspension of the threads 2 and 3, tubular elements may be associated, such as those represented by the numbers 17 and 18, which will allow the threads 3 and 4 to be guided, avoiding lateral chafing on the walls of the chamber 1, which could result in damage or breakage.

Figure 4:
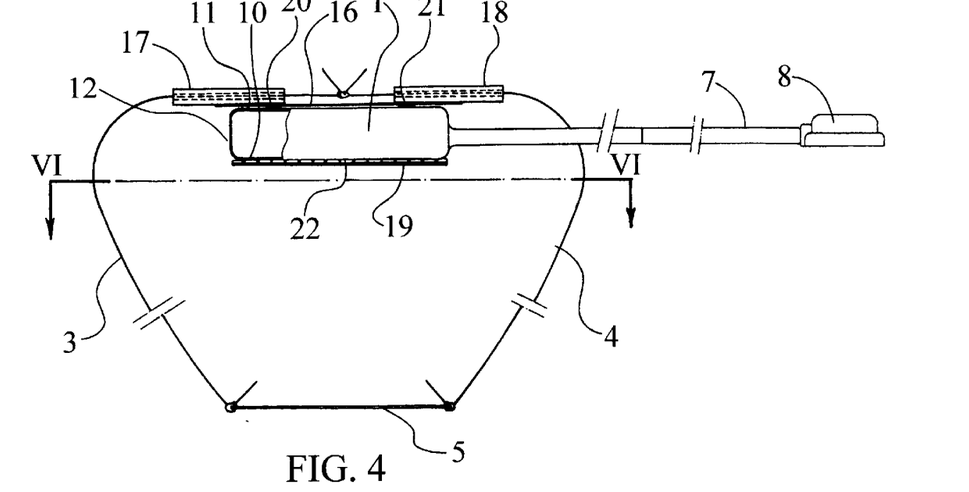
FIGS. 4 and 5 show different views in lateral elevation and in plan of a device produced in accordance with the present invention, with the chamber unexpanded.
Figure 5:
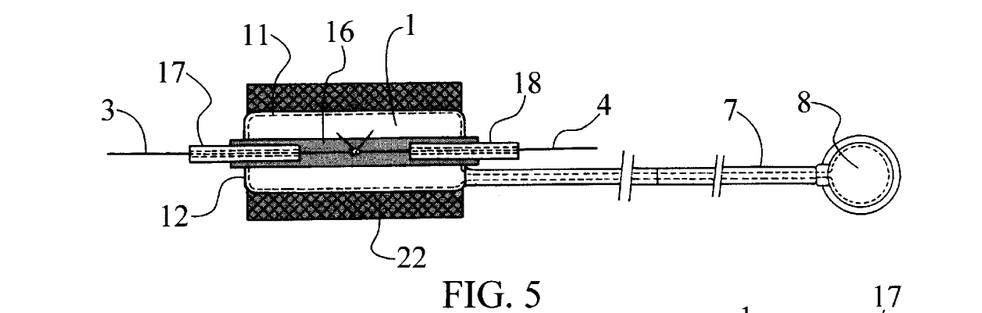
Figure 6:
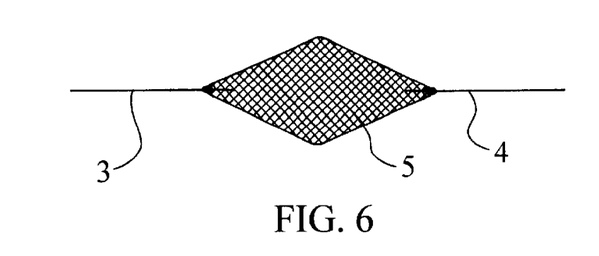
FIG. 6 shows a plan view of an embodiment of the sling used for raising purposes.
Figure 7:
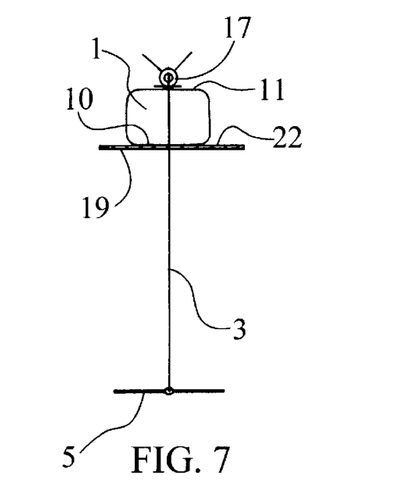
FIG. 7 is a simplified side view which shows the position of the expandable chamber, the lower support plate, connection threads and sling.
Figure 8:
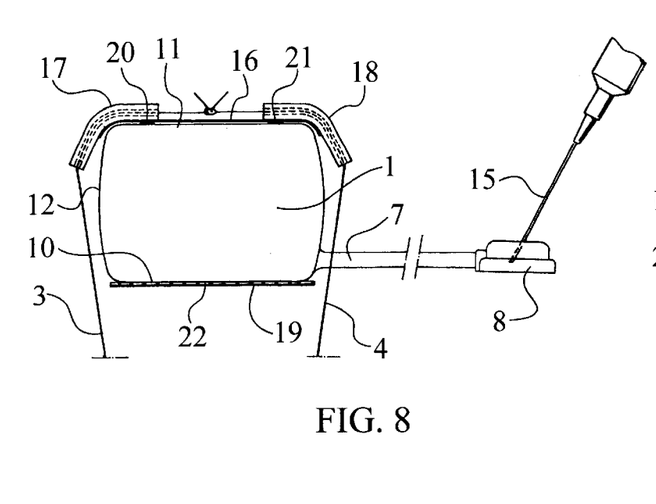
FIG. 8 is a simplified view showing the introduction of liquid under low pressure by means of an specific capsule, representing the chamber in its expanded form.
Figure 9:
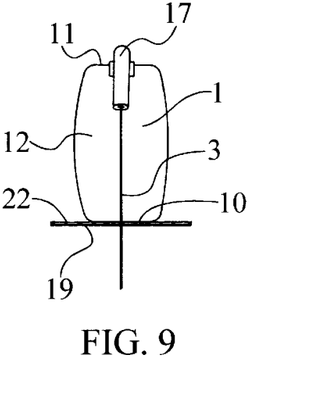
FIG. 9 shows a simplified side view corresponding to FIG. 8.
Figure 10:
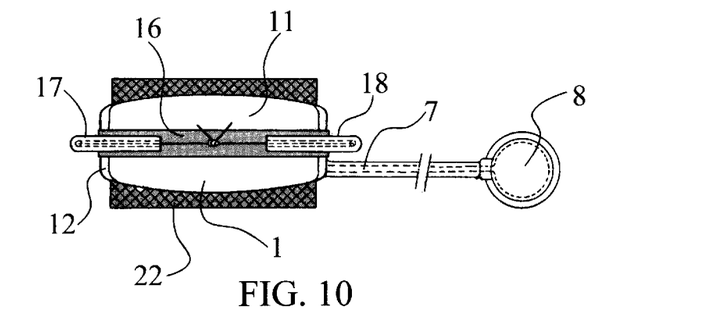
FIG. 10 shows a plan view of the elements of FIG. 8 with the chamber in an expanded situation.

As will be understood, by means of the device which is the subject of the present invention, it will be very easy to introduce a liquid into the inside of the elastic chamber 1 for the purpose of increasing the distance which separates the upper and lower bases 10 and 11 of the main chamber of the device or also to extract said liquid in order to reduce the separation between the bases. The said effects will respectively result in tensioning or slackening of the threads 3 and 4. As can be seen in FIGS. 4 and 5, the elastic chamber 1, apart from carrying at the top the plate of titanium or other suitable material 16, may also similarly have at the bottom a second plate 19 intended to improve the characteristics of seating of the device in the part of the anatomy intended to contain it. The base 19 may also be associated to an intermediate grid-like web 22 located between the support plate and the lower base of the expandable chamber 1. Said support plate 19 may be made out of titanium as well.

Figure 11:
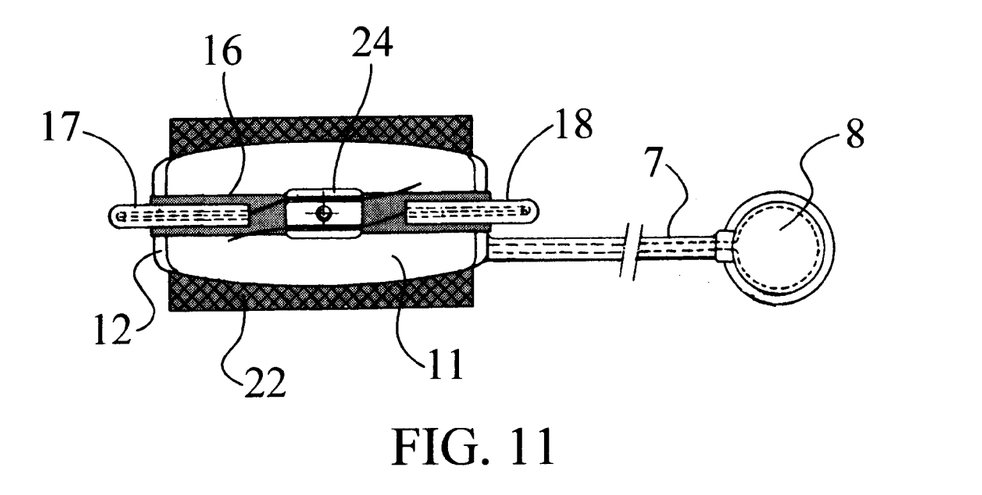
FIGS. 11 and 12 show, respectively, a plan view and a front view of a variant for the fastening of the suspension threads.
Figure 12:
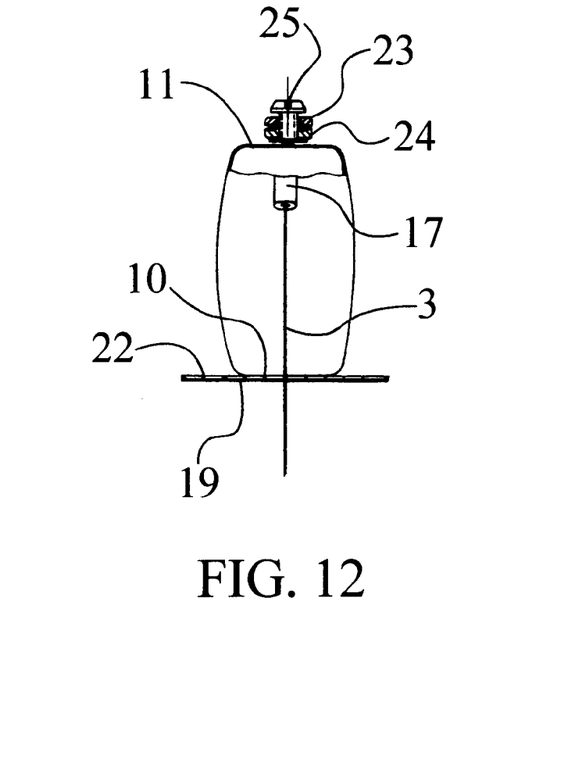

Although the fastening of the threads 3 and 4 has been represented in the figures preferably my means of fixing knots on the upper base of the expandable chamber, said fastening could also be carried out by means of flat fixing clamp as shown in FIGS. 11 and 12, in which said clamp is comprised of the two parts 23 and 24, between which the threads are clamped. To this end said plates may have small guiding grooves. The fastening is carried out by means of a screw 25 or other similar means.

Although the invention has been defined above with reference to a concrete exemplary embodiment, it may also exhibit numerous alternative forms within the essential concepts claimed. In particular, it should be understood that the precise structure of the chamber may vary widely, assuming different geometric shapes, such as parallelepipedal, cylindrical, oval, conical or prismatic shapes, etc. Likewise, the number of threads for suspension of the anatomical organs, as well as the precise points of suspension thereof, may vary within wide limits.

What is claimed is:

1. A device for adjusting the height of internal organs comprising an elastic chamber the volume of which varies in relation to the amount of a fluid received in said container, said chamber being sized to be received within a selected area of the body, at least one thread connected to said container and adapted to be connected with a body part whereby changes in the volume of said chamber causes movement of said thread to affect consequent movement of the body part, a subcutaneous capsule adapted to be located close to the skin of a patient, and a tube connecting said capsule with said chamber, whereby the introduction or removal of a fluid from said capsule causes variations in the volume of said chamber.

2. A device as in claim 1, and a fluid for filling said chamber, said fluid carrying a contrasting component.

3. A device as in claim 2, wherein said fluid is water.

4. A device as in claim 1, wherein said elastic chamber comprises two opposed bases, the first base being adapted to sit on a selected anatomical region, said second base being connected to said thread for suspension of the selected body part.

5. A device as in claim 4, wherein said elastic chamber has unidirectional deformation characteristics.

6. A device as in claim 5, wherein the lateral walls of said elastic chamber are stronger than said base walls to permit unidirectional deformation in the direction of separation of said first and second bases from each other.

7. A device as in claim 4, wherein the elastic chamber is provided with high strength plates on said first and second bases.

8. A device as in claim 7, and a web comprising a grid between said first base and said plate provided thereon.

9. A device as in claim 7, wherein the plate connected to said second base is rigidly connected thereto.

10. A device as in claim 7, wherein said plates are made of titanium.

11. A device as in claim 1, and tubular elements positioned adjacent said chamber and receiving said thread therethrough to prevent damage to the walls of said chamber.

12. A device as in claim 1, wherein said thread comprises high strength, biocompatible synthetic material.

13. A device as in claim 1, and a hypodermic needle for introducing or extracting the liquid from said capsule.

14. A device as in claim 1, wherein the ends of said thread are attached to said elastic chamber.

* * * * *

UNITED STATES PATENT AND TRADEMARK OFFICE
CERTIFICATE OF CORRECTION

PATENT NO.    : 6,117,067
DATED         : September 12, 2000
INVENTOR(S)   : Josè Ma Gil-Vernet Vila It is certified that error appears in the above-identified patent and that said Letters Patent is hereby corrected as shown below:

Title page,
Item [76], Inventor, please correct the name of the inventor from "Josè Ma Gil-Vernet" to read:
-- Josè Ma GIL-VERNET VILA --

Signed and Sealed this

Nineteenth Day of February, 2002

Attest:

Attesting Officer

JAMES E. ROGAN
Director of the United States Patent and Trademark Office